United States Patent [19]

Buchmann et al.

[11] Patent Number: 5,891,910
[45] Date of Patent: *Apr. 6, 1999

[54] 9-HALOGEN-(Z) PROSTAGLANDIN DERIVATIVES, PROCESS FOR THEIR PRODUCTION AND THEIR USE AS PHARMACEUTICAL AGENTS

[75] Inventors: Bernd Buchmann; Werner Skuballa; Helmut Vorbrueggen; Bernd Raduechel; Olaf Loge; Walter Elger; Claus-Steffen Stuerzebecher; Karl-Heinz Thierauch, all of Berlin, Germany

[73] Assignee: Schering Aktiengesellschaft, Germany

[ * ] Notice: The term of this patent shall not extend beyond the expiration date of Pat. No. 5,506,166.

[21] Appl. No.: 467,888

[22] Filed: Jun. 6, 1995

Related U.S. Application Data

[60] Continuation of Ser. No. 313,667, Sep. 27, 1994, which is a division of Ser. No. 838,658, Feb. 21, 1992, abandoned, which is a continuation of Ser. No. 709,053, Jun. 3, 1991, abandoned, which is a continuation of Ser. No. 588,522, Sep. 25, 1990, abandoned, which is a continuation of Ser. No. 383,773, Jul. 24, 1989, abandoned, which is a continuation of Ser. No. 220,291, Jul. 18, 1988, abandoned.

[30] Foreign Application Priority Data

Jul. 17, 1987 [DE] Germany .......................... 37 24 189.3
Jul. 17, 1987 [DE] Germany .......................... 37 24 190.7

[51] Int. Cl.⁶ ....................... C07C 405/00; A61K 31/557
[52] U.S. Cl. ......................... 514/530; 514/573; 560/121; 562/503
[58] Field of Search ........................... 560/121; 562/503; 514/530, 573

[56] References Cited

U.S. PATENT DOCUMENTS

| | | |
|---|---|---|
| 3,936,487 | 2/1976 | Nelson . |
| 3,980,694 | 9/1976 | Bundy . |
| 4,423,067 | 12/1983 | Skuballa et al. . |
| 4,444,788 | 4/1984 | Skuballa et al. . |
| 4,454,339 | 6/1984 | Skuballa et al. . |
| 4,692,464 | 9/1987 | Skuballa et al. . |
| 4,708,963 | 11/1987 | Skuballa et al. . |
| 4,789,685 | 12/1988 | Skuballa .................................. 560/118 |
| 4,971,987 | 11/1990 | Vorbueggen ............................. 560/118 |
| 5,004,752 | 4/1991 | Raduechel et al. . |
| 5,079,259 | 1/1992 | Skuballa .................................. 560/118 |

FOREIGN PATENT DOCUMENTS

| | | |
|---|---|---|
| 11591 | 5/1980 | European Pat. Off. . |
| 55208 | 6/1982 | European Pat. Off. . |
| 69696 | 1/1983 | European Pat. Off. . |
| 30377 | 2/1984 | European Pat. Off. . |
| 1269657 | 4/1972 | United Kingdom . |
| 86/05488 | 9/1986 | WIPO . |

OTHER PUBLICATIONS

Schulz et al., "Cardio–and Hemodynamic Profile . . . ", Advances in Pros. Throm. and leuk. Res., vol. 21, 1990.
J. of Med. Chem., vol. 29, No. 3, Comm. to the Ed., Mar. 1986.
J. Westwick, "The effect of pulmonary metabolites of prostaglandins $E_1$, $E_2$, . . . ", Proceed. of the B.P.S., 15th–16th Jul., 1976.

*Primary Examiner*—Robert Gerstl
*Attorney, Agent, or Firm*—Millen, White, Zelano & Branigan, P.C.

[57] ABSTRACT

The invention relates to 9-halogen-(Z) prostane derivatives of formula I

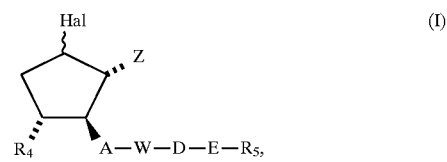

in which Z represents the radicals
Hal represents a chlorine or fluorine atom,
$R_1$ represents $$-\overset{O}{\underset{\|}{C}}-OR_2$$

$$-\overset{O}{\underset{\|}{C}}-NHR_3$$

A represents a —$CH_2$—$CH_2$—, a trans—CH=CH or —C≡C—,
W represents a free or a functionally modified $$\begin{array}{c} CH_3 \\ | \\ C \\ | \\ OH \end{array}$$

group,

D and E together represent a direct bond or
D represents a straight-chain alkylene group with 1–10 C atoms, a branched-chain alkylene group with 2–10 C atoms or an annular alkylene group with 3–10 C atoms, which optionally can be substituted by fluorine atoms, and
E represents an oxygen or sulfur atom, a direct bond, a C≡C bond or a —$CR_6$=$CR_7$ group, and $R_6$ and $R_7$ are different and mean a hydrogen atom, a chlorine atom or a $C_1$–$C_4$ alkyl group,
$R_4$ represents a free or functionally modified hydroxy,
$R_5$ means a hydrogen atom, an alkyl, a halogen-substituted alkyl, a cycloalkyl or an optionally substituted aryl or a heterocyclic group.

18 Claims, No Drawings

9-HALOGEN-(Z) PROSTAGLANDIN DERIVATIVES, PROCESS FOR THEIR PRODUCTION AND THEIR USE AS PHARMACEUTICAL AGENTS

This is a continuation, of the application Ser. No. 08/313,667 filed Sep. 27, 1994, which is a divisional of Ser. No. 07/838,658, filed Feb. 21, 1992, abandoned, which is a continuation of application Ser. No. 07/709,053, filed Jun. 3, 1991, abandoned, which is a continuation of Ser. No. 07/588,522 filed Sep. 25, 1990, abandoned, which is a continuation of Ser. No. 07/383,773 filed Jul. 24, 1989, abandoned, which is a continuation of application Ser. No. 07/220,291, filed Jul. 18, 1988 abandoned.

BACKGROUND OF THE INVENTION

This invention relates to new 9-halogen(Z) prostaglandin derivatives, a process for their product and their use as pharmaceutical agents.

Form the very extensive prior art of prostaglandins and their analogs it is known that this class of substances because of its biological and pharmacological properties is suitable for treating mammals, including man. However, its use as a pharmaceutical agent often runs into difficulties. Most natural prostaglandins have too short a duration of effect for therapeutic purposes, since they are metabolically broken down too quickly be various enzymatic processes. All structural changes have the aim of increasing the duration of effect and the selectivity of the effectiveness.

SUMMARY OF THE INVENTION

An object of the invention is to provide novel 9-halogen-(Z) prostaglandin derivatives having outstanding specificity of action, better effectiveness and prolonged duration of effect as compared to natural prostaglandins and their derivatives and which are especially suitable for oral application.

Upon further study of the specification and appended claims, further objects and advantages of this invention will become apparent to those skilled in the art.

The invention relates to 9-halogen-(Z) prostaglandin derivatives of the formula I (I) [structure with Hal, Z, $R_4$, A—W—D—E—$R_5$]

in which Z represents the radicals

[structures] $R_1$ or [structure with O—$R_1$]

Hal represents a chlorine or fluorine atom in the alpha or beta position, $R_1$ represents the radical $CH_2OH$ or $$-C(=O)-OR_2$$

with $R_2$ meaning a hydrogen atom, an alkyl, cycloalkyl, aryl or heterocyclic radical or $R_1$ represents the radical $$-C(=O)-NHR_3$$

with $R_3$ meaning an acid residue or the radical $R_2$ and

A represents a —$CH_2$—$CH_2$—, a trans—CH=CH or —C≡C— group,

W represents a free or a functionally modified hydroxymethylene group or a free or functionally modified $$\underset{OH}{\overset{CH_3}{\underset{|}{C}}}$$

group, and the respective OH groups can be in the alpha or beta position,

D and E together represent a direct bond or

D represents a straight-chain alkylene group with 1–10 C atoms, a branched-chain alkylene group with 2–10 C atoms or an annular alkylene group with 3–10 C atoms, which optionally can be substituted by fluorine atoms, and E represents an oxygen or sulfur atom, a direct bond, a—C≡C— bond or a —$CR_6$=$CR_7$ group, and $R_6$ and $R_7$ are different and mean a hydrogen atom, a chlorine atom or a $C_{1-C4}$ alkyl group, $R_4$ represents a free or functionally modified hydroxy group, $R_5$ means a hydrogen atom, an alkyl, a halogen-substituted alkyl, a cycloalkyl, an optionally substituted aryl or a heterocyclic group, and if $R_2$ means a hydrogen atom, its salts with physiologically compatible bases or its cyclodextrin chlathrates.

Straight-chain or branched-chain alkyl groups with 1–10 C atoms such as, for example, methyl, ethyl, propyl, butyl, isobutyl, tert-butyl, pentyl, neopentyl, hexyl, heptyl, decyl are suitable as alkyl groups $R_2$. Alkyl groups $R_2$ can optionally be substituted singly to multiply by halogen atoms, alkoxy groups, optionally substituted aryl or aroyl groups, dialkylamino and trialkylammonium, and a single substitution is to be preferred. As substituents there can be mentioned. e.g., fluorine, chlorine or bromine, phenyl, dimethylamino, diethylamino, methoxy, ethoxy. As preferred alkyl groups $R_2$ are to be mentioned those with 1–4 C atoms such as, e.g., methyl, ethyl, propyl, dimethylaminopropyl, isobutyl, butyl.

Suitable as aryl groups $R_2$ are both substituted and unsubstituted aryl groups such as, for example, phenyl, 1-naphthyl and 2-naphthyl, which in each case can be substituted by 1–3 halogen atoms, a phenyl group, 1–3 alkyl groups with 1–4 C atoms in each case, a chloromethyl, fluoromethyl, trifluoromethyl, carboxyl, hydroxy or alkoxy group with 1–4 C atoms. Substituents in the 3 and 4 position on the phenyl ring, for example, by fluorine, chlorine, alkoxy or trifluoromethyl or in the 4 position by hydroxy are preferred.

The cycloalkyl group $R_2$ can contain 3–10, preferably 5 and 6, carbon atoms in the ring. The rings can be substituted alkyl groups with 1–4 carbon atoms. For example, there can be mentioned cyclopentyl, cyclohexyl or methylcyclobexyl.

Suitable as heterocyclic groups $R_2$ are 5- and 6-membered heterocycles, which contain at least one heteroatom, preferably nitrogen, oxygen or sulfur. For example, there can be mentioned 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, etc.

Suitable as acid radicals are physiologically compatible acid radicals. Organic carboxylic acids and sulfonic acids with 1–15 carbon atoms are suitable, which belong to the aliphatic, cycloaliphatic, aromatic, aromatic aliphatic and heterocyclic series. These acids can be saturated, unsaturated and/or polybasic and/or substituted in a conventional manner. Alkyl, hydroxy, alkoxy, oxo or amino groups or halogen atoms can be mentioned as examples for the substituents. For example, the following carboxylic acids can be mentioned: formic acid, acetic acid, propionic acid, butyric acid, isobutyric acid, valerianic acid, isovalerianic acid, caproic acid, heptanoic acid, caprylic acid, pelargonic acid, capric acid, undecylic acid, lauric acid, tridecylic acid, myrisitic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di and tri-chloroacetic acid, aminoacetic acid, diethylaminoacetic acid, piperidinoacetic acid, morpholinoacetic acid, lactic acid, succinic acid, adipic acid, benzoic acid, with halogen, trifluoromethyl, hydroxy, alkoxy or carboxy groups substituted benzoic acids, nicotinic acid, isonicotinic acid, furan-2-carboxylic acid, cyclopentylpropionic acid. As preferred acyl radicals those are suitable with up to 10 carbon atoms. Sulfonic acids are, for example, alkanesulfonic acids with 1–10 C atoms are suitable such as, e.g., methanesulfonic acid, ethanesulfonic acid, isopropanesulfonic acid and butanesulfonic acid as well as beta-chloroethanesulfonic acid, cyclopentanesulfonic acid, cyclohexanesulfonic acid, benzenesulfonic acid, p-toluenesulfonic acid, p-chlorobenzene- sulfonic acid, N,N-dimetbylaminosulfonic acid, N,N-diethylamino- sulfonic acid, N,N-bis(beta-chloroethyl)-aminosulfonic acid, N,N-diisobutylaminosulfonic acid, N,N-dibutylaminosulfonic acid, pyrrolidino-, piperidino-, piperazino-, N-methylpiperazino- and morpholino- sulfonic acid. Acyl radicals and alkanesulfonic acids with 1–4 C atoms are preferred.

The hydroxy groups in W and $R_4$ can be functionally modified, for example, by etherification or esterification, and also the modified hydroxy group in W can be in the alpha or beta position, and free hydroxy groups are preferred.

Radicals known to those of ordinary skill in the art are suitable as ether and acyl radicals. Preferred are easily cleavable ether radicals such as, for example, the tetrahydropyranyl, tetrahydrofuranyl, alpha-ethoxyethyl, trimethylsilyl, dimethyl tert-butylsilyl, dimethyl thexylsilyl, diphenyl tert-butylsilyl and tribenzylsilyl radical. As suitable acyl radicals the same ones are suitable as mentioned for $R_3$ under organic carboxylic acids, namely, there can be mentioned, for example, acetyl, propionyl, butyryl and benzoyl.

As alkyl and alkenyl groups $R_5$ suitable are straight-chain or branched-chain alkyl radicals with 1–10 C atoms and alkenyl radicals with 2–10 C atoms, especially 1–6 and 2–6 C atoms, which optionally can be substituted by substituents phenyl, alkyl with 1–4 C atoms or halogen. There can be mentioned, for example, methyl, ethyl, propyl, isobutyl, tert-butyl, pentyl, hexyl, heptyl, octyl, butenyl, isobutenyl, propenyl, pentenyl, hexenyl as well as benzyl, and for the case, that D and E together mean a direct bond, optionally alkinyl with 2–6 C atoms substituted in the 1 position by fluorine or $C_{1-C4}$ alkyl. Suitable as alkinyl radicals are: ethinyl, propin-1-yl, propin-2-yl, 1-methylpropin-2-yl, 1-fluoropropin-2-yl, 1-ethylpropin-2-yl, 1-fluorobutin-2-yl, butin-2-yl, butin-3-yl, 1-methylbutin-3-yl, 1-methyl-3-yl, 1-fluoropentin-3-yl, 1-methylpentin-2-yl, 1-fluoropentin-2-yl, 1-methylpentin-4-yl, 1-fluoropentin-4-yl, hexin-1-yl, 1-methylhexin-2-yl, 1-fluorohexin-2-yl, 1-methylhexin-3-yl, 1-methylhexin-4-yl, hexin-3-yl, 1,1-dimethylpropin-2-yl, 1,1-dimethylbutin-3-yl, 1,1-dimethylpentin-3-yl, 1,1-dimethylpentin-4-yl, 1,1-dimethylhexin-3-yl, 1,1-dimethylhexin-4-yl, etc.

Bromine, chlorine and fluorine are suitable as halogen substituents of alkyl or alkenyl groups $R_5$. Chlorine and fluorine are preferred.

Cycloalkyl groups $R_5$ can contain 3–10, preferably 3–6 carbon atoms, in the ring. The rings can be substituted by alkyl groups with 1–4 carbon atoms. There can be mentioned, for example, cyclopropyl, cyclobutyl, cyclopentyl, cyclohexyl and methylcyclohexyl.

Suitable as substituted or unsubstituted aryl groups $R_5$ are for example: phenyl, 1-naphthyl and 2-naphthyl, which in each case can be substituted by 1–3 halogen atoms, a phenyl group, 1–3 alkyl groups with 1–4 C atoms in each case, a chloromethyl, fluoromethyl, trifluoromethyl, carboxyl, alkoxy, or hydroxy group. Substitution in the 3 and 4 position on the phenyl ring is preferred, for example, by fluorine, chlorine, alkoxy or trifluormethyl or in the 4 position by hydroxy.

Suitable as heterocyclic groups $R_5$ are 5- and 6-membered heterocycles, which contain at least 1 heteroatom, preferably nitrogen, oxygen or sulfur. There can be named, for example: 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, etc.

Suitable as alkylene group D are straight-chain, branched-chain, annular*, saturated and/or unsaturated alkylene radicals, preferably saturated with 1–10, especially 1–5 C atoms, which optionally can be substituted by fluorine atoms. There can be mentioned, for example: methylene, fluoromethylene, difluoromethylene, ethylene, 1,2-propylene, ethylethylene, trimethylene, tetramethylene, pentamethylene, 1,1-difluoroethylene, 1-fluoroethylene, 1-methyl tetramethylene, 1-methyl trimethylene, 1-methylene ethylene, 1-methylene tetramethylene, 1-methyl trimethylene, 2-methyl tetramethylene,

* By "annular" is meant $C_2$–$C_9$-alkylene substituted by $C_1$–$C_8$-alkylene forming a ring, bonded to a single carbon atom of the $C_{2-9}$-alkylene group or to two different, preferably adjacent, carbon atoms of the $C_{2-9}$-alkylene group. 1,1-trimethylene ethylene, 1,2-methylene ethylene. If a double bond is present, it is in the 2, 3 or 4 position in the alkylene radicals.

Inorganic and organic bases are suitable for salt formation, as they are known to a man of the art for formation of physiologically compatible salts. There can be mentioned, for example, alkali hydroxides such as sodium and potassium hydroxide, alkaline-earth hydroxides such as calcium hydroxide, ammonia, amines such as ethanolamine, diethanolamine, triethanolamine, N-methylglucamine, morpholine, tris-(hydroxymethyl)methylamine, etc.

The invention further relates to a process for the production of 9-halogen-(Z) prostane derivatives of formula I according to the invention, characterized in that in a way known in the art a compound is reacted of formula II

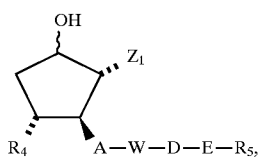  (II)

in which $Z_1$ means the radicals

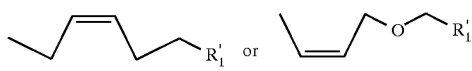

which can be the 9-OH group in alpha or beta position and $R_1'$ represents the radical

with $R_2$ meaning alkyl, cycloalkyl, aryl or heterocyclic radical

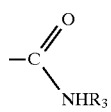

with $R_3$ meaning an acid radical, an alkyl, cycloalkyl, aryl or a heterocyclic radical and A, D, E and $R_5$ have the meanings already indicated above, after previous protection of the free OH groups in $R_4$ and W.

a) by an intermediate sulfonic acid ester with a halide of general formula III, $R_8X$ <span style="float:right">(III)</span> in which $R_8$ has the meaning of lithium, sodium, potassium or tetraalkyl or trialkylbenzyl ammonium with alkyl as saturated $C_1$–$C_6$ radical and X meaning fluorine or chlorine, or b) with the reagent diethylaminosulfur trifluoride (DAST) to the compounds of formula I in which Hal is a fluorine atom in the alpha or beta position or with carbon tetrachloride or hexachloroethane/ triphenylphosphine to the compounds of formula I in which Hal is a chlorine atom in the alpha or beta position, and then in any sequence protected hydroxide groups are freed and/or free hydroxy groups are esterified or etherified and/or double bonds are hydrogenated and/or an esterified carboxyl group

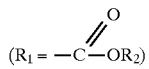

is saponified and/or a free carboxyl group ($R_2$=H) is converted into an amide

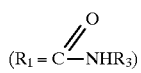

or salt and/or a free or esterified carboxyl group

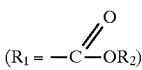

is reduced.

The reaction of the compounds of formula II to the compounds of formula I takes place first by conversion with a sulfonic acid chloride or sulfonic acid anhydride into a sulfonic acid ester in a way known in the art and then reaction with a halide of formula III in an inert solvent as, for example, benzene, toluene, diethyl ether, tetrahydrofuran, methylene chloride, acetonitrile, dimethylformamide at temperatures between 0° C. and 100° C., preferably 20° C. to 70° C.

The reaction of the compounds of formula II to the compounds of formula I with carbon tetrachloride and triphenylphosphine or hexachloroethane/triphenylphophine takes place in an inert solvent such as, for example, dimethylformamide, dimethylacetamide, acetonitrile, methylene chloride at temperatures between 0° C. and 80° C., preferably 20° C. to 45° C. in the presence of a base such as, for example, pyridine, triethylamine, etc.

The reaction of the compounds of formula II to the compounds of formula I with Hal meaning a fluorine atom takes place with diethylaminosulfur trifluoride in a solvent such as, for example, dichloromethane at temperatures between −120° C. and 0° C., preferably at −70° C., optionally in the presence of a tertiary base such as, for example, pyridine.

If an alcohol of formula II with a 9-hydroxy group in beta position is used, compounds of formula I with a halogen atom in the 9-alpha position are obtained, if an alcohol with a hydroxy group in alpha position is used, compounds with a halogen atom in the 9-beta position are obtained.

Reduction to the compounds of formula I with $R_1$ meaning a $CH_2OH$ group is performed with a reduction agent such as, for example, lithium aluminum anhydride, diisobutyl aluminum hydride, etc., suitable for the reduction of esters of carboxylic acids. Suitable as solvents are diethyl ether, tetrahydrofuran, dimethoxyethane, toluene, etc. The reduction is performed at temperatures of −30° C. to the boiling temperature of the solvent used, preferably 0° C. to 30° C.

Freeing of the functionally modified hydroxy groups takes place according to known methods. For example, cleavage of hydroxy protecting groups such as, for example, the tetrahydropyranyl radical, in an aqueous solution of an organic acid such as, e.g., oxalic acid, acetic acid, propionic acid, etc., or in an aqueous solution of an inorganic acid such as, e.g., hydrochloric acid. To improve the solubility, an inert organic solvent miscible with water is suitably used. Suitable organic solvents are, e.g., alcohols such as methanol and ethanol, and ethers such as dimethoxyethane, dioxane and tetrahydrofuran. Tetrahydrofuran is preferably used. Cleavage is preferably performed at temperatures between 20° C. and 80° C.

Saponification of the acyl groups takes place, for example, with alkali or alkaline-earth carbonates or hydroxides in an alcohol or in an aqueous solution of an alcohol. Suitable as alcohols are aliphatic alcohols such as, e.g., methanol, ethanol, butanol, etc., preferably methanol. As alkali carbonates and hydroxides there can be mentioned potassium and sodium salts. The potassium salts are preferred.

Suitable as alkaline-earth carbonates and hydroxides are, for example, calcium carbonate, calcium hydroxide and barium carbonate. The reaction takes place at −10° C. to +70° C., preferably at +25° C.

The introduction of the ester group

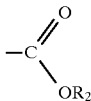

for $R_1$, in which $R_2$ represents an alkyl group with 1–10 C atoms, takes place according to the methods known in the art. The 1-carboxy compounds, for example, are reacted with diazocarbons in a way known in the art. Esterification with the diazohydrocarbons takes place, e.g., by a solution of the diazohydrocarbon in an inert solvent, preferably in diethyl ether, being mixed with 1-carboxy compounds in the same or in another inert solvent such as, e.g., methylene chloride. After the reaction has ended in 1 to 30 minutes, the solvent is removed and the ester purified in the usual way. Diazoalkanes are either known or can be produced according to known methods [Org. Reactions, Vol. 8, pp. 389–394 (1954)].

Introduction of the ester group

for $R_1$, in which $R_2$ represents a substituted or unsubstituted aryl group, takes place according to methods known to those of ordinary skill in the art. For example, the 1-carboxy compounds are reacted with the corresponding aryl hydroxy compounds with dicyclohexylcarbodiimide in the presence of a suitable base, for example pyridine, DMAP, triethylamine, in an inert solvent. Suitable as solvents are methylene chloride, ethylene chloride, chloroform. The reaction is performed at temperatures between −30° C. and +50° C., preferably at 10° C.

The prostaglandin derivatives of formula I with $R_2$ meaning a hydrogen atom can be converted with suitable amounts of the corresponding inorganic bases under neutralization into a salt. For example, the solid inorganic salt is obtained by dissolving of the corresponding PG acids in water, which contains a stoichiometric amount of the base, after evaporation of the water or after addition of a solvent miscible with water, e.g., alcohol or acetone.

For production of an amine salt, which takes place in the usual way, the PG acid, e.g., is dissolved in a suitable solvent, for example, ethanol, acetone, diethyl ether, acetonitrile or benzene and at least the stoichiometric amount of the amine is added to this solution. In this case, the salt usually precipitates in solid form or is isolated after evaporation of the solvent in the usual way.

Introduction of the amide group

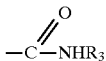

for $R_1$ takes place according to methods known in the art. The carboxylic acids of formula I ($R_2$=H) are first converted in the presence of a tertiary amine such as, for example, triethylamine, with chloroformic acid isobutyl ester into the mixed anhydride. Reaction of the mixed anhydride with the alkali salt of the corresponding amide or with ammonia ($R_3$=H) or of the corresponding amine takes place in an inert solvent or solvent mixture such as, for example, tetrahydrofuran, dimethoxyethane, dimethylformamide, hexamethylphosphoric acid triamide at temperatures between −30° C. and +60° C., preferably at 0° C. to 30° C.

Another possibility for the introduction of the amide group

for $R_1$ with $R_3$ meaning an acid radical consists in the reaction of a 1-carboxylic acid of formula I ($R_2$=H), in which hydroxy groups optionally are intermediately protected, with compounds of formula IV

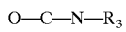   (IV)

in which $R_3$ has the above-indicated meaning.

Reaction of the compound of formula I ($R_2$=H) wish an isocyanate of formula IV takes place optionally with addition of a tertiary amine such as, e.g., triethylamine or pyridine. The reaction can be performed without solvent or in an inert solvent, preferably acetonitrile, tetrahydrofuran, acetone, dimethylacetamide, methylene chloride, diethyl ether, toluene, at temperatures between −80° C. and 100° C., preferably at 0 to 30° C.

If the initial product contains OH groups in the prostane radical, these OH groups are also brought to reaction. Finally if end products are desired that contain free hydroxyl groups in the prostane radical, a start is made from initial products in which these are intermediately protected by preferably easily cleavable ether or acyl radicals.

The compounds of formula II serving as initial material with a 9-alpha hydroxy group and $Z_1$ as

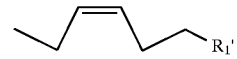

are either known or can be produced according to the process indicated in DE-OS 2317019 and 2320552.

The compounds of formula II serving as initial material with a 9-alpha hydroxy group and $Z_1$ as

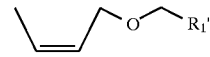

can be produced, for example, by a lactone of formula V in a way known in the art

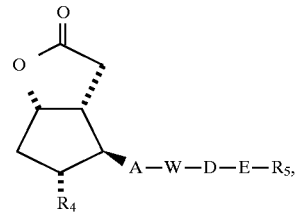   (V)

in which A, D, E and $R_5$, which have the meanings already indicated and the OH groups present in $R_4$ and W are provided with a basic-resistant protecting group such as, e.g., by etherification with dihydropyran, by treatment with bases such as, for example, sodium hydroxide, and then careful acidification are converted into the hydroxy acids of formula VI:

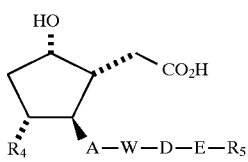

After esterification of the acid with diazomethane and etherification of the free OH group with dimethyl tert-butylsilyl chloride, the ester in a way known in the art is either reduced directly to the aldehydes of formula VII

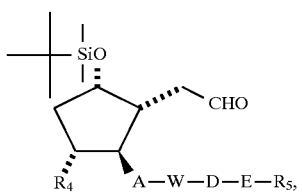

or first is reduced to the corresponding alcohols and then oxidized to the aldehydes of formula VII.

By reaction of these aldehydes with tetrabromomethane/triphenylphosphine in the presence of zinc and treatment of the resulting raw products with butyllithium, the alkines of formula VIII is attained

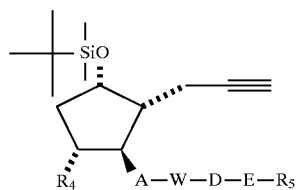

After metalation of the alkines of formula VIII, for example with butyllithium, and reaction with formaldehyde, the resulting propargyl alcohols are etherified under basic conditions with bromoacetic acid tert-butyl ester and yield the esters of formula IX.

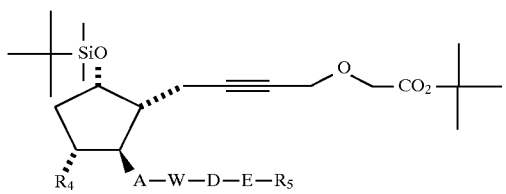

By Lindlar hydrogenation of the alkine esters of formula IX and then selective cleavage of the silyl protecting groups in the 9 position the compounds of formula II with a alpha hydroxy group are obtained serving as initial material.

The compounds of formula II with a 9-beta hydroxy group are obtained from the 9-alpha hydroxy compounds by an inversion reaction as described, e.g., in Synthesis, 292–294 (1980).

The new prostaglandin analogs are marked by a considerable stability in comparison with PGE derivatives.

The new prostaglandin analogs of formula I are valuable pharmaceutical agents, since in a similar activity spectrum they exhibit a substantially improved (higher specificity) and especially substantially prolonged action than the corresponding natural prostaglandins.

The active ingredients according to the invention show a cytoprotective and ulcer-healing effect, inhibit gastric acid secretion and thus counteract the undesirable sequelae of nonsteroid anti-inflammatory substances. Moreover, they act cytoprotectively on the liver, kidneys and also the pancreas.

The new prostaglandin analogs act strongly luteolytically, i.e., for triggering a luteolysis substantially smaller doses are needed than in the case of the corresponding natural prostaglandins.

For inducing abortions, especially after oral or intravaginal application, substantially smaller amounts of the new prostaglandin analogs are necessary in comparison with the natural prostaglandins.

During registration of the isotonic uterus contractions on anesthetized rats and on the isolated rat uterus it is shown that the substances according to the invention are substantially more effective and their actions last longer than in the case of natural prostaglandins. The new prostaglandin derivatives are suitable, after a single enteral or parenteral application, for inducing a menstruation or interrupting a pregnancy. Further they are suitable for synchronization of the sexual cycle of female mammals such as rabbits, cows, mares, sows, etc. Further, the prostaglandin derivatives according to the invention are suitable for cervix dilation as preparation for diagnostic or therapeutic operations.

The good tissue specificity of the antifertilely active substances is shown in research on other smooth muscle organs such as, for example, guinea pig ileum or on the isolated rabbit trachea, where substantially less stimulation can be observed than by natural prostaglandins. The substances according to the invention also have a bronchospasmolytic action. Further, they also cause a shrinking of the nasal mucous membrane.

For inducing abortions, especially after oral or intravaginal application, substantially smaller amounts of the new prostaglandin analogs are necessary in comparison with the natural prostaglandins.

Some of the compounds are effective in lowering blood pressure, in regulating cardiac dysrhythmia and in inhibiting platelet aggregation with the resulting possibilities of use such as, e.g., in coronary heart disease and myocardial infarction. The new prostaglandins can also be used in combination, e.g., with beta-blockers, diuretics, phosphodiesterase inhibitors, calcium antagonists, thromboxane antagonists, thromboxane synthetase inhibitors and cyclooxygenase inhibitors, anticoagulant substances such as fibrinolytic agents, leukotriene antagonists, leukotriene synthetase inhibitors and antigestagens.

The new prostaglandin analogs have a great affinity for receptors in membrane preparations from brains and as a result of their properties can serve for influencing psychic processes such as, e.g., sleep.

A comparison of $^3$H-PGD$_2$ and (5Z,13E)-(9R,11R,15,S)-9-dichloro-3-oxa-15-cyclodioxyl-11,15-dihydroxy-16,17,18,19,20-pentan or -5,13-prostadienic acid (A) in the receptor test showed a competition factor of 6.5. The compound A lowered also the blood pressure after i.v.-application in comparison with (5Z,13E)-(9R,11R,15,S)-9-chloro-15-cyclodioxyl-11,15-dihydroxy-16,12,18,19,20-pentan or -5,13-prostadienic acid (a compound from WO 86/05488) more than twice as effectively.

The dosage of the compounds is 1–1500 micrograms/kg/day, if they are administered to, e.g., mammals including human patients.

For medical use the active ingredients can be converted into a form suitable for inhalation, for oral, parenteral or local (e.g., vaginal) application. Aerosol solutions are suitably produced for inhalation.

Tablets, dragees or capsules, for example, are suitable for oral application.

Sterile, injectable, aqueous or oil solutions are used for parenteral administration.

Suppositories, for example, are suitable and customary for vaginal application.

The invention thus also relates to pharmaceutical agents on the basis of the compounds of formula I and the usual auxiliary agents and carriers, including cyclodextrin clathrates.

The active ingredients according to the invention are to serve in combination with auxiliary agents, which are usual and known in galenicals, e.g., for the production of preparations for inducing an abortion, for cycle control, for inducing a birth, for treatment of hypertonia or for treatment of gastrointestinal disorders such as, e.g., for healing of gastric or duodenal ulcers. For this purpose but also for other uses the preparations can contain 0.01–100 mg of active compound.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

Example 1

(4Z, 13E)-(9R,11R,15R)-9-chloro-11,15-dihydroxy-16,16-dimethyl-4,13-prostadienoic acid methyl ester 319 mg of methane sulfonic acid chloride is added at 0° C. to a solution of 1.00 g of (4Z,13E)-(9S,11R,15R)-9-hydroxy-16,16-dimethyl-11,15-bis-(tetrahydropran-2-yloxy)-4,13-prostadienic acid methyl ester in 10 ml of pyridine. It is stirred for 4 hours at 20° C. and the solution is added to a suspension of 9.99 g of tetrabutylammonium chloride in 10 ml of toluene. After 15-hours stirring at 0° C., it is stirred for another 7 hours at 40° C. Then it is added to 100 ml of ice water and extracted three times with 50 ml each of ether. After the organic phase is washed twice with 20 ml of brine, dried over $MgSO_4$ and is concentrated by evaporation in a vacuum a residue is obtained which is chromatographed on silica gel with hexane/0–40% ether. 839 mg of oily (4Z,13E)-(9R,11R,15R)-9-chloro-16,16-dimethyl-11,15-bis(tetrahydropyran-2-yloxy)-4,13-prostadienoic acid methyl ester is obtained. For cleavage of the protecting groups, the resulting ester is stirred with 31 ml of a mixture of acetic acid/water/ tetrahydrofuran (65/35/10) for 24 hours at 20° C. After addition of toluene and concentration of the solution by evaporation in a vacuum the residue is chromatographed on silica gel. With toluene/0–10% isopropanol as eluant, 326 mg of the title compound is obtained as colorless oil.

IR ($CHCl_3$): 3600, 3420, 2945, 1730, 1021, 977/cm.

The 9alpha alcohol used as initial material is obtained as follows:

1a) (5 EZ, 13E)-(9S, 11R, 15R)-9-hydroxy-5-methoxy-16,16-11,15-bis-(tetrahydropyran-2-yloxy)-1,2,3,4-tetranor-5,13-protadiene 10.6 g of potassium tert-butylate is added to a solution of 32.5 g of (methoxymethyl)-triphenylphosphonium chloride in 135 ml of a mixture of dimethyl sulfoxide and tetrahydrofuran in a ratio of 2:1 at 0° C. and stirred for 30 minutes at 0° C.

Then a solution of 7.15 g of (2RS,3aR,4R,5R,6aS)-4-[(E)-(3R)-4,4-dimethyl-3-((tetrahydropyran-2-yloxy)-1-octenyl]-5-(tetrahydropyran-2-yl-oxy)-perhydrocyclopenta[b]furan-2-ol is instilled in 56 ml of tetrahydrofuran. It is stirred for 3.5 hours at 20° C., then added to 300 ml of brine, extracted three times with 200 ml each of ether, dried over $MgSO_4$ and concentrated by evaporation in a vacuum. The oily residue is chromatographed on silica gel with hexane/0–50% ethyl acetate. 7.83 g of the title compound is obtained as oil.

IR ($CHCl_3$): 3510, 2950, 1655, 1022, 977/cm.

1b) (5EZ,13E)-(9S,11R,15R)-9-acetoxy-5-methoxy-16,16-dimethyl-11,15-bis-(tetrahydropyran-2-yloxy-1,2,3,4,-tetranor-5,13-prostadiene 4.8 ml of acetic anhydride is added to a solution of 7.83 g of (5EZ,13E)-(9S,11R,15R)-9-hydroxy-5-methoxy-16,16-dimethyl-11,15-bis-(tetrahydropyran-2-yloxy-1,2,3,4-tetranor-5,13- in 9.6 ml of pyridine at 0° C. and is stirred for 20 hours at 20° C. Then it is concentrated by evaporation in a vacuum and the oily residue is chromatographed on silica gel with hexane/0–30% ethyl acetate. 7.72 g of the title compound is obtained as oil. IR ($CHCl_3$): 2945, 1730, 1657, 1022, 975/cm.

1c) (13E)-(9S,11R,15R)-9-acetoxy-11,15-dihydroxy-16,16-dimethyl-2,3,4,5-tetranor-13-prostenal.

A solution of 7.72 g of (5EZ,13E)-(9S,11R,15R)-9-acetoxy-5-methoxy-16,16-dimethyl-11,15-bis-(tetrahydropyran-2-yloxy)-1,2,3,4-tetranor-5,13-prostadiene in 345 ml of mixture of acetic acid/water/tetrahydrofuran (65/35/10) is stirred for 20 hours at 40° C. After addition of toluene and concentration of the solution in a vacuum, the residue is chromatographed on silica gel with hexane/0–50% ethyl acetate and 4.98 g of the title compound is obtained as oil.

IR ($CHCl_3$): 3605, 3425, 2963, 2935, 2233, 1728, 1020, 973/cm.

1d) (13E)-(9S,11R,15R)-9-acetoxy-16,16-dimethyl-11,15-bis-(tetrahydropyran-2-yloxy)-2,3,4,5-tetranor-13-prostenal 5.14 ml of dihydropyran and 46 mg of p-toluenesulfonic acid are added at 0° C. to a solution of 4.98 g of (13E)-(9S,11R,15R)-9-acetoxy-11,15-dihydroxy-16,16-dimethyl-2,3,4,5-tetranor-13-prostenal in 145 ml of methylene chloride. After 1-hour stirring at 20° C., 0.1 ml of triethylamine is added and it is allowed to stir for 15 minutes more at 20° C. After concentration of the solution by evaporation in a vacuum, the residue is chromatographed on silica gel with hexane/0–30% ethyl acetate and 5.43 g of the title compound is obtained as oil.

IR ($CHCl_3$): 2950, 2230, 1725, 1020, 975/cm.

1e) (2RS,4aR,5R,6R,7aS)-5[(E)-(3R)-4,4-dimethyl-3-(tetrahydropyran-2-yloxy)-1-octenyl]-6-(tetrahydropyran-2-yloxy)-perhydrocyclopenta[b]pyran-2-ol 2.13 g of anhydrous potassium carbonate is added to a solution of 5.43 g of (13E)-(9S,11R,15R)-9-acetoxy-16,16-dimethyl-11,15-bis-(tetrahydropyran-2-yloxy)-2,3,4,5-tetranor-13-prostenal in 120 ml of methanol at 20° C. and then stirred for 20 hours at this temperature. The pH is adjusted to 6 with citric acid and the solution is concentrated by evaporation in a vacuum. The residue is taken up in 200 ml of methylene chloride, washed twice with 30 ml each of brine and dried on $MgSO_4$. After concentration of the solution by evaporation in a vacuum, the residue is chromatographed on silica gel with hexane/0–30% ethyl acetate and 4.43 g of the title compound is obtained as oil.

IR ($CHCl_3$): 3600, 3420, 2945, 1020, 977/cm.

1f) (4Z,13E)-(9S,11R,15R)-9-hydroxy-16,16-dimethyl-11,15-bis-(tetrahydropyran-2-yloxy)-4,13-prostadienoic acid methyl ester 108 g of potassium tert-butylate is added to a solution of 23.7 g of (3-carboxypropyl)-triphenylphosphinum bromide in 81 ml of a mixture of dimethyl sulfoxide and tetrahydrofuran in a ratio of 2:1 at 0° C. and is stirred for 30 minutes at 0° C. A solution of 4.43 g of (2RS,4aR,5R,6R,7aS)-5[(E)-(3R)-4,4-dimethyl-3-(tetrahydropyran-2-yloxy)-1-octenyl]-6-(tetrahydropyran-2-yloxy)-perhydropenta[b]pyran-2-ol is instilled in 33 ml of tetrahydrofuran and is stirred for 3 hours at 20° C. It is added to 500 ml of ice water, acidified with citric acid to pH 4 and extracted several times with methylene chloride. The organic extract is then washed with brine, dried over MgSO$_4$ and concentrated by evaporation in a vacuum. The residue is dissolved with 210 ml of methylene chloride. It is treated for 15 minutes with excess ethereal diazomethane and the solution is concentrated to dryness by evaporation. The oily residue is chromatographed on silica gel with hexane/0–90% ether. 4.61 g of the title compound is obtained as oil.

IR (CHCl$_3$): 3600, 2950, 1735, 1022, 977/cm.

Example 2

(4Z,13E)-(9S,11R,15R)-9-chloro-11,15-dihydroxy-16,16-dimethyl-4,13-prostadienoic acid methyl ester Analogously to example 1, 185 mg of the title compound is obtained as oil from 612 mg of (4Z,13E)-(9R,11R,15R)-9-hydroxy-16,16-dimethyl-11,15-bis-(tetrahydropyran-2-yloxy)-4,13-prostadienoic acid methyl ester.

IR (CHCl$_3$): 3600, 3420, 2960, 1735, 1022, 976/cm.

The 9beta alcohol used as initial material is produced as follows:

2a) (4Z,13E)-(9R,11R,15R)-9-hydroxy-16,16-dimethyl-11,15-bis-(tetrahydropyran-2-yloxy)-4,13-prostadienoic acid methyl ester 715 mg of p-toluenesulfonic acid chloride is added to a solution of 1.05 g of (4Z,13E)-(9S,11R,15R)-9-hydroxy-16,16-dimethyl-11,15-bis-(tetrahydropyran-2-yloxy)-4,13-prostadienoic acid methyl ester in 16 ml of pyridine at 0° C. After 1 hour, the ice bath is removed and it is allowed to stand for 48 hours at 20° C. Then it is again cooled to 0° C., mixed with 0.1 ml of water and stirred for 1 hour. For working up, it is diluted with ice-cold ether, shaken successively with ice-cold 10% sulfuric acid, sodium bicarbonate solution and brine, dried over MgSO$_4$ and concentrated by evaporation in a vacuum. 1.43 g of oily 9-tosylate is obtained, which is dissolved in 50 ml of dimethyl sulfoxide, mixed with 3.7 g of potassium nitrite and heated 3 hours at 80° C. Then it is diluted with water, extracted with ether, the extract is washed with brine, dried over MgSO$_4$ and concentrated by evaporation in a vacuum. The residue is purified by chromatography on silica gel with hexane/0–50% ethyl acetate and 612 mg of the title compound is obtained as oil.

IR (CHCl$_3$): 3600, 3415, 2945, 1735, 1020, 977/cm.

Example 3

(4Z,13E)-(9R,11r,15R)-9-chloro-aa,15-dihydroxy-16,16-dimethyl-4,13-prostadienoic acid 400 mg of potassium hydroxide dissolved in 5 ml of water is added to a solution of 326 mg of (4Z,13E)-(9R,11R,15R)-9-chloro-11,15-dihydroxy-16,16-dimethyl-4,13-prostadienoic acid methyl ester in 15 ml of methanol and allowed to stir for 4 hours at 20° C. After concentration by evaporation in a vacuum it is diluted with 70 ml of water, acidified with citric acid to pH 4 and extracted several times with ethyl acetate. The extract is washed with brine, dried over MgSO$_4$ and concentrated by evaporation in a vacuum. The residue is purified by chromatography on silica gel with methylene chloride/0–90% acetone and 215 mg of the title compound is obtained as oil.

IR (CHCl$_3$): 3600, 3400, 2955, 1712, 1020, 975/cm.

Example 4

(4Z,13E)-(9R,11R,15R)-9-chloro-11,15-dihydroxy-16-phenoxy-17,18,19,20-tetranor-4,13-prostadienoic acid methyl ester Analogously to example 1, 470 mg of the title compound is obtained as colorless oil from 1.48 g of (4Z,13E)-(9S,11R,15R)-9-hydroxy-16-phenoxy-11,15-bis-(tetrahydropyran-2-yloxy)-17,18,19,20-tetranor-4,13-prostadienoic acid methyl ester.

IR (CHCl$_3$): 3600, 3425, 2958, 1732, 1600, 1585, 1020, 977/cm.

The initial material for the production of the title compound is obtained from (2RS,3aR,4R,5R,6aS)-4-[(E)-(3R)-4-phenoxy-3-(tetrahydropyran-2-yloxy)-1-butenyl]-5-(tetrahydropyran-2-yloxy)-perhydrocyclopenta[b]furan-2-ol according to example 1a.

Example 5

(4Z,13E)-(9R,11R,15R)-9-chloro-11,15-dihydroxy-16-phenoxy-17,18,19,20-tetranor-4,13-prostadienoic acid Analogously to example 3, 411 mg of the title compound is obtained as oil from 470 mg of (4Z,13E)-(9E,11R,15R)-9-chloro-11,15-dihydroxy-16-phenoxy-17,18,19,20-tetranor-4,13-prostadienoic acid methyl ester.

IR (CHCl$_3$): 3600, 3420, 2948, 1712, 1600, 1587, 1022, 977/cm.

Example 6

(4Z,13E)-(9R,11R,15R)-9-fluoro-11,15-dihydroxy-16,16-dimethyl-4,13-prostadienoic acid methyl ester 0.56 ml of diethylaminosulfur trifluoride (DAST) is instilled in a solution of 2.05 g of (4Z,13E)-(9S,11R,15R)-9-hydroxy-16,16-diethyl-11,15-bis-(tetrahydropyran-2-yloxy)-4,13-prostadienoic acid methyl ester in 43 ml of methylene chloride and 1.1 ml of pyridine at −70° C. and stirred for 3.5 hours at −70° C. Then it is added to 200 ml of 5% sodium bicarbonate solution cooled to 0° C. and allowed to stir vigorously for 10 minutes. Then it is extracted several times with methylene chloride, the extract is washed with water, dried over MgSO$_4$ and concentrated by evaporation in a vacuum. The residue is stirred for 24 hours at 20° C. with 60 ml of a mixture of acetic acid/water/tetrahydrofuran (65/35/10), concentrated by evaporation in a vacuum after addition of toluene and the raw product is purified by chromatography on silica gel with toluene/0–10% isopropanol. 306 mg of the title compound is obtained as oil.

IR (CHCl$_3$): 3605, 3420, 2958, 1732, 1018, 975/cm.

Example 7

(4Z,14E)-(9R,11R,15R)-9-fluoro-11,15-dihydroxy-16,16-dimethyl-4,13-prostadienoic acid Analogously to example 3, 252 mg of the title compound is obtained as oil from 306 mg of (4Z,13E)-(9R,11R,15R)-9-fluoro-11,15-dihydroxy-16,16-dimethyl-4,13-prostadienoic acid methyl ester.

IR (CHCl$_3$): 3600, 3420, 2950, 1710, 1020, 977/cm.

Example 8

(5Z,13E)-(9R,11R,15S)-9-chloro-15-cyclohexyl-11,15-dihydroxy-3-oxa-16,17,18,19,20-pentanor-5,13-prostadienoic acid tert-butyl ester 2.32 g of oily (5Z,13E)-(9R,11R,15S)-9-chloro-15-cyclohexyl-3-oxa-11,15-bis-(tetrahydropyran-2-yloxy)-16,17,18,19,20-pentanor-5,13-prostadienoic acid tert-butyl ester is obtained from 2.54 g of (5Z,13E)-(9S,11R,15S)-15-cyclohexyl-9-hydroxy-3-oxa-11,15-bis-(tetrahydropyran-2-yloxy)-16,17,18,29,20-pentanor-5,13-prostadienoic acid tert-butyl ester and 773 mg of methanesulfonic acid chloride analogously to example 1. Cleavage of the protecting groups takes place analogously to example 1. With methylene chloride/0.5% acetone as eluant, 915 mg of the title compound is obtained as colorless oil.

IR (CHCl$_3$): 3605, 3410, 2928, 1742, 1020, 974/cm.

The 9alpha alcohol used as initial material is obtained as follows:

8a) (13E)-(9S, 11R, 15S)-15-cyclohexyl-9-(tert-butyldimethylsilyloxy)-11,15-bis-(tetrahydropran-2-yloxy)-2,3,4,5,6,16,17,18,19,20-decanor-13-prostenoic acid methyl ester 56 ml of a 1 N aqueous sodium hydroxide solution is added to a solution of 6.45 g of (3aR, 4R, 5R, 6aS)-4-[(E)-(3S)-3-cyclohexyl-3-(tetrahydropyran-2-yloxy)-1-propenyl]-5-(tetrahydropyran-2-yloxy)-perhydrocyclopenta[b]furan-2-one in 56 ml of methanol and is stirred for 24 hours at 20° C. Then the methanol portion is removed by concentration in a vacuum and the resulting aqueous solution is adjusted to pH 4.5 with cold 10% sulfuric acid. Then it is first extracted with 400 ml of methylene chloride/ethyl acetate (1/1) and then twice more with 100 ml each of ethyl acetate. The organic extracts are washed neutral with brine, dried over MgSO$_4$ and concentrated by evaporation in a vacuum. The residue is dissolved in 63 ml of methylene chloride, treated for 15 minutes with excess ethereal diazomethane and the solution is concentrated to dryness in a vacuum. The oily residue is dissolved in 73 ml of dimethylformamide and, after addition of 3.51 g of imidazole and 3.88 g of tert-butyldimethylsilyl chloride, is stirred for 4 hours at 20° C. Then the reaction mixture is diluted with 600 ml of hexane/ether (1/1), washed with 100 ml of water and then washed neutral with brine. It is dried over MgSO$_4$, concentrated by evaporation in a vacuum and chromatographed on silica gel with hexane/0–30% ethyl acetate. 5.89 g of the title compound is obtained as oil.

IR (CHCl$_3$): 2930, 1728, 1018, 975/cm.

8b) (13E)-(9S, 11R, 15S)-15-cyclohexyl-9-(tert-butyldimethylsilyloxy-11,15-bis-(tetrahydropyran-2-yloxy)-2,3,4,5,6,16,17,18,19,20-decanor-13-prostenal 24.2 ml of a 1.2 molar DIBAH solution in toluene is instilled in a solution of 5.76 g of (13E)-(9S, 11R, 15S)-15-cyclohexyl-9-(tert-butyldimtethylsilyloxy)-11,15-bis-(tetrahydropran-2-yloxy)-2,3,4,5,6,16,17,18,19,20-decanor-13 prostenoic acid methyl ester in 240 ml of toluene at –70° C. and is stirred for two more hours at this temperature. Then 3 ml of isopropanol is added, stirred for 10 minutes, to instill then 12 ml of water. After removal of the cold bath, after 3-hours stirring at 20° C. it is filtered from the resulting precipitate and rewashed with ethyl acetate. The filtrate is concentrated to dryness by evaporation and the residue is chromatographed on silica gel with hexane/0–40% ethyl acetate. 4.15 g of the title compound is obtained as oil.

IR (CHCl$_3$): 2930, 2725, 1718, 1020, 972/cm.

8c) (13E)-(9S,11R,15S)-15-cyclohexyl-9-(tert-butyldimethylsilyloxy)-11,15-bis-(tetrahydropran-2-yloxy)-1,2,3,4,16,17,18,19,20-monanor-13-prosten-5-in 7.20 g of triphenylphosphine is added a suspension of 9.09 g of tetrabromomethane and 1.79 g of zinc powder in 180 ml of methylene chloride at 20° C. and is stirred for 24 hours at this temperature. Then 3.59 g of (13E)-(9S, 11R, 15S)-15-cyclohexyl-9-(tert-butyldimethylsilyloxy)-11,15-bis-(tetrahydropyran-2-yloxy)-2,3,4,5,6,16,17,18,19,20-decanor-13-prostenal is instilled in 37 ml of methylene chloride and is stirred for 1.5 hours at 20° C. Then the mixture is added to 2 liters of pentane with stirring, filtered and the filtrate is concentrated by evaporation in a vacuum.

The oily residue is dissolved in 143 ml of tetrahydrofuran, 10.9 ml of a 1.6-molar butyllithium solution in hexane is instilled at –70° C. and stirred for 1 hour at this temperature. Then it is allowed to warm to 20° C. and stirred once more for 1 hour. Then it is concentrated by evaporation in a vacuum, diluted with 300 ml of ether and washed neutral with brine. After drying over Na$_2$SO$_4$ it is concentrated by evaporation in a vacuum. The resulting residue is chromatographed with hexane/0–20% ethyl acetate as eluant on silica gel. 4.34 of the title compound is obtained as oil.

IR (CHCl$_3$): 3210, 2930, 970/cm.

8d) (13E)-(9S, 11R, 15S)-15-cyclohexyl-9-(tert-butyldimethylsiloxy)-11,15-bis-(tetrahydropyran-2-yloxy)-2,3,4,16,17,18,19,20-octanor-13-prosten-5-inol 9.6 ml of a 1.6-molar butyllithium solution in hexane is instilled to a solution of 4.33 g of (13E)-(9S, 11R, 15S)-15-cyclohexyl-9-(tert-butdimenthylsilyloxy)-11,15-bis-(tetrahydropyran-2-yloxy)-1,2,3,4,16,17,18,19,20-nonanor-13-prosten-5-in in 51 ml of tetrahydrofuran at –20° C. and is stirred for 1 hour at –20° C. Then 468 mg of dried paraformaldehyde is added and stirred for 90 minutes at 0° C. Then it is diluted with 50 ml of water and extracted three times with 50 ml each of ether. The organic extracts are washed twice with 50 ml each of brine, dried over Na$_2$SO$_4$ and concentrated by evaporation in a vacuum. The residue is chromatographed on silica gel with hexane/0–30% ethyl acetate. 3.11 of the title compound is obtained as oil.

IR (CHCl$_3$): 3610, 3425, 2930, 1020, 977/cm.

8e) (13E)-(9S, 11R, 15S)-15-cyclohexyl-3-oxa-9-(tert-butyldimethylsilyloxy)-11,15-bis-(tetrahydropyran-2-yloxy)-16,17,18,19,20-pentanor-13-prosten-5-inic acid tert-butyl ester To a solution of 1.72 g of (13E)-(9S, 11R, 15S)-15-cyclohexyl-9-(tert-butyldimethylsilyloxy)-11,15-bis-(tetrahydropyran-2-yloxy)-2,3,4,16,17,18,19,20-octanor-13-prosten-5-inol in 22 ml of toluene are added 2.84 g of bromoacetic acid tert-butyl ester, 8.8 ml of 25% sodium hydroxide solution and 42 mg of tetrabutylammonium hydrogen sulfate. After 16-hours of stirring at 20° C., it is diluted with 100 ml of ether and acidified with citric acid to pH 6. It is extracted three times with 50 ml each of ether, the combined organic phases are washed with brine and dried over MgSO$_4$. After concentration by evaporation in a vacuum, the residue is chromatographed on silica gel with hexane/0–20% ethyl acetate. 1.65 g of the title compound is obtained as oil.

IR (CHCl$_3$): 2937, 1745, 1020, 977/cm.

8f) (5Z, 13E)-(9S, 11R, 15S)-15-cyclohexyl-3-oxa-9-(tert-butyldimethylsilyloxy)-11,15-bis-(tetrahydropyran-2-yloxy)16,17,18,19,20-pentanor-5,13-prostadienoic acid tert-butyl ester A mixture of 1.73 g of (13E)-(9S, 11R, 15S)-15-cyclohexyl-3-oxa-9-(tert-butyldimethylsilyloxy)-11,15-bis-(tetrahydropyran-2-yloxy)-16,17,18,19,20-pentanor-13-prosten-5-inic acid tert-butyl ester and 519 mg of Lindlar catalyst in 480 ml of toluene is stirred in a hydrogen atmosphere. After absorption of an equivalent of hydrogen it is filtered. After concentration of the filtrate in a vacuum, the residue is chromatographed on silica gel. With hexane/0–20% ethyl acetate as eluant, 1.74 g of the title compound is obtained as oil.

IR (CHCl$_3$): 2930, 1745, 1020, 976/cm.

8g) (5Z, 13E)-9S, 11R, 15S)-15-cyclohexyl-9-hydroxy-3-oxa-11,15-bis-(tetrahydropyran-2-yloxy)-16,17,18,19,20-pentanor-5,13-prostadienoic acid tert-butyl ester 3.24 g of (5Z, 13E)-(9S, 11R, 15S)-15-cyclohexyl-3-oxa-9-(tert-butyldimethylsilyloxy)-11,15-bis-(tetrahydropyran- 2-yloxy)-16,17,18,19,20-pentanor-5,13-prostadienoic acid tert-butyl ester is added to 18.3 ml of a 1-molar tetrabutylammonium fluoride solution in tetrahydrofuran and stirred for 2 hours at 20° C. It is mixed with 150 ml of water and extracted twice with 100 ml each of methylene chloride. The organic extracts are washed with brine, dried over MgSO₄ and concentrated by evaporation in a vacuum. The resulting residue is chromatographed on silica gel with hexane/0–50% ethyl acetate. 2.54 g of the title compound is obtained as oil. IR (CHCl₃): 3600, 3480, 2930, 1743, 974/cm.

Example 9

(5Z, 13E)-(9R, 11R,15S)-9-chloro-15-cyclohexyl-11,15-dihydroxy-3-oxa-16,17,18,19,20-pentanor-5,13-prostadienoic acid 7.7 ml of a 0.5 normal sodium hydroxide solution is added to a solution of 857 mg of (5Z, 13E)-(9R, 11R, 15S)-9-chloro-15-cyclohexyl-11,15-dihydroxy-3-oxa-16,17,18,19,20-pentanor-5,13-prostadienoic acid tert-butyl ester in 7.7 ml of methanol and stirred for 18 hours at 20° C. It is diluted with 50 ml of water and acidified with citric acid to pH 5. It is extracted three times with 50 ml each of methylene chloride, dried over MgSO₄ and concentrated by evaporation in a vacuum. The residue is chromatographed on silica gel with methylene chloride/0–15% acetone. 75 mg of the title compound is obtained as oil. IR (CHCl₃): 3605, 3410, 2930, 1738, 1020, 973/cm.

Example 10

(5Z,13E)-(9S, 11R, 15S)-9-chloro-15-cyclohexyl-11,15-dihydroxy-3-oxa-16,17,18,19,20-pentanor-5,13-prostadienoic acid Analogously to examples 8 and 9, the title compound is obtained as oil from (5Z, 13E)-(9R, 11R, 15S)-15-cyclohexyl-9-hydroxy-3-oxa-11,15-bis-(tetrahydropyran-2-yloxy)-16,17,18,19, 20-pentanor-5,13-prostadienoic acid tert-butyl ester. IR (CHCl₃): 3605, 3420, 2930, 1740, 1022, 975/cm.

The 9beta alcohol used as initial material is obtained as follows:

10a) (5Z, 13E)-(9R, 11R, 15S)-15-cyclohexyl-9-hydroxy-3-oxa-11,15-bis-(tetrahydropyran-2-yloxy)-16,17,18,19,20-pentanor-5,13-prostadienoic acid tert-butyl ester 1.71 g of p-toluenesulfonic acid chloride is added to a solution of 2.68 g of (5Z, 13E)-(9S, 11R, 15S)-15-cyclohexyl-9-hydroxy-3-oxa-11,15-bis-(tetrahydropyran-2-yloxy)-16,17,18, 19,20-pentanor-5,13-prostadienoic acid tert-butyl ester in 37 ml of pyridine at 0° C. After 1 hour the ice bath is removed and it is allowed to stand for 48 hours at 20° C. Then it is cooled again to 0° C., mixed with 0.2 ml of water and stirred for 1 hour. For working up it is diluted with ice-cold ether, successively shaken with ice-cold 10% sulfuric acid, sodium bicarbonate and brine, dried over MgSO₄ and concentrated by evaporation in a vacuum. The resulting oily 9-tosylate is dissolved in 120 ml of dimethyl sulfoxide, mixed with 9 g of potassium nitrite and heated for 3 hours to 80° C. It is then diluted with water, extracted with ether, the extract is washed with brine, dried over MgSO₄ and concentrated by evaporation in a vacuum. The residue is purified by chromatography on silica gel with hexane/0–50% ethyl acetate as eluant and 1.63 g of the title compound is obtained as oil. IR (CHCl₃): 3605, 3460, 2935, 1745, 1022, 975/cm.

Example 11

(5Z, 13E)-(9R, 11R, 15R)-9-chloro-11,15-dihydroxy-16,16-dimethyl-3-oxa-5,13-prostadienoic acid Analogously to examples 8 and 9, the title compound is obtained as oil from (5Z, 13E)-(9S, 11R, 15R)-9-hydroxy-16,16-dimethyl-3-oxa-11,15-bis-(tetrahydropyran-2-yloxy)-5,13-prostadienoic acid tert-butyl ester.

IR (CHCl₃): 3600, 3400, 2935, 1740, 1020, 977/cm.

The initial material for the production of the title compound is obtained according to example 8a from (2RS, 3aR, 4R,5R,6aS)-4-[(E)-(3R)-4,4-dimethyl-3-(tetrahydropyran-2-yloxy)-1-octenyl]-5-(tetrahydropyran-2-yloxy)-perhydrocyclopenta [b]furan-2-ol.

Example 12

(5Z, 13E)-(9R, 11R, 15S)-15-cyclohexyl-9-fluoro-11,15-dihydroxy-3-oxa-16, 17, 18, 19, 20-pentanor-5,13-prostadienoic acid 0.3 ml of diethylaminosulfur trifluoride (DAST) is added to a solution of 1.31 g of (5Z, 13E)-(9S, 11R, 15S)-15-cyclohexyl-9-hydroxy-3-oxa-11,15-bis-(tetrahydropyran-2-yloxy)-16,17,18, 19,20-pentanor-5,13-prostadienoic acid tert-butyl ester in 20 ml of methylene chloride and 0.5 ml of pyridine at −70° C. and after 15 minutes 0.1 ml of DAST is added once more. After another 15 minutes it is mixed with 50 ml of 5% sodium bicarbonate solution, the cold bath is removed, it is stirred vigorously for 10 minutes at 20° C., then extracted with methylene chloride, the extract is washed with brine, dried over MgSO₄ and concentrated by evaporation in a vacuum. The residue is stirred for 24 hours at 20° C. with 20 ml of a mixture of acetic acid/water/tetrahydrofuran (65/35/10), it is concentrated by evaporation in a vacuum after addition of toluene and the raw product is purified by chromatography on silica gel with toluene/0–10% isopropanol. (5Z, 13E)-(9R, 11R, 15R)-15-cyclohexyl-9-fluoro-11,15-dihydroxy-3-oxa-16,17,18,19, 20-pentanor-5,13-prostadienoic acid tert-butyl ester is obtained, which analogously to example 9 is saponified. 52 mg of the title compound is obtained as oil. IR (CHCl₃): 3600, 3410, 2930, 1740, 1022, 977/cm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 9-halogen-(Z) prostane derivative of the formula

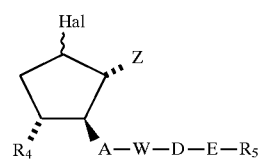

in which

Hal is a chlorine or fluorine atom in alpha or beta position,

Z is

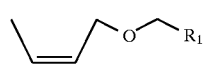

$R_1$ is

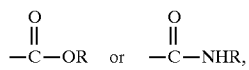

wherein R is (a) hydrogen; (b) C-alkyl; (c) C-alkyl substituted by halogen, $C_{1-4}$-alkoxy, $C_{6-10}$-aryl, $C_{6-10}$-aroyl, $C_{6-10}$-aryl or $C_{6-10}$ aroyl each substituted as defined below for aryl, dialkylamino or trialkylammonium; (d) $C_{3-10}$-cycloaklyl or C3–10-cycloalkyl substituted by $C_{1-4}$-alkyl; (e) $C_{6-10}$-aryl or $C_{6-10}$-aryl substituted by 1–3 halogen atoms, phenyl, 1–3 $C_{1-4}$-alkyl groups, chloromethyl, fluoromethyl, trifluoromethyl, carboxyl, hydroxy or $C_{1-4}$-alkoxy; (f) a 5- or 6-membered aromatic heterocyclic ring containing an N, O or S atom;

$R_3$ is an acyl group of a $C_{1-5}$-hydrocarbon carboxylic or sulfonic acid, or a group defined for $R_2$;

A is a —$CH_2$—$CH_2$—, a trans—CH=CH— or —C≡C— group,

W is hydroxymethylene or

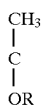

wherein the hydroxy and OR group can be in the alpha or beta position,

D and E together are a single bond;

$R_4$ is OR;

R is H; an acyl group of a $C_{1-15}$-hydrocarbon carboxylic or sulfonic acid; tetrahydropyranyl; tetrahydrofuranyl; alpha-ethoxyethyl; trimethylsilyl; dimethyl tert-butylsilyl; dimethyl hexylsilyl; diphenyl tert-butylsilyl or tribenzylsilyl;

$R_5$ is $C_{3-10}$-cycloalkyl or $C_{3-10}$-cycloalkyl substituted by $C_{1-4}$-alkyl; $C_{6-10}$-aryl or $C_{6-10}$-aryl substituted by 1–3 halogen atoms, phenyl, 1–3 $C_{1-4}$-alkyl, chloromethyl, fluoromethyl, trifluoromethyl, carboxyl, hydroxy or $C_{1-4}$-alkoxy; or a 5- or 6-membered aromatic heterocyclic ring containing a N, O or S atom;

or where $R_2$ is H, a physiologically compatible salt thereof or a cyclodextrin clathrate thereof.

2. A compound according to claim 1, wherein $R_2$ is $C_{1-4}$-alkyl; phenyl 3- or 4-substituted by F, Cl, $C_{1-4}$-alkoxy or trifluoromethyl; phenyl 4-substituted by hydroxy; or $C_{5-6}$-cycloalkyl.

3. A compound according to claim 1, wherein $R_2$ is 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl or 2-tetrazolyl.

4. A compound according to claim 1, wherein $R_3$ is an acyl group of a $C_{1-10}$-hydrocarbon carboxylic or $C_{1-10}$-alkanesulfonic acid.

5. A compound according to claim 1, wherein $R_3$ is an acyl group of a $C_{1-4}$-hydrocarbon carboxylic or $C_{1-4}$-alkanesulfonic acid.

6. A compound according to claim 1, wherein $R_3$ is an acyl group of formic acid, acetic acid, propionic acid, butyric acid, isobutyric acid, valerianic acid, isovalerianic acid, caproic acid, heptanoic acid, caprylic acid, pelargonic acid, capric acid, undecylic acid, lauric acid, tridecylic acid, myrisitic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di or tri-chloroacetic acid, aminoacetic acid, diethylaminoacetic acid, piperidinoacetic acid, morpholinoacetic acid, lactic acid, succinic acid, adipic acid, benzoic acid, nicotinic acid, isonicotinic acid, furan-2-carboxylic acid, cyclopentylpropionic acid, methanesulfonic acid, ethanesulfonic acid, isopropanesulfonic acid, butanesulfonic acid, beta-chloroethanesulfonic acid, cyclopentanesulfonic acid, cyclohexanesulfonic acid, benzenesulfonic acid, p-toluenesulfonic acid, p-chlorobenzene- sulfonic acid, N,N-dimethylaminosulfonic acid, N,N-diethylamino- sulfonic acid, N,N-bis(beta-chloroethyl)-aminosulfonic acid, N,N-diisobutylamino-sulfonic acid, N,N-dibutylaminosulfonic acid, or pyrrolidino-, piperidino-, piperazino-, N-methylpiper-azino- or morpholino- sulfonic acid.

7. A compound according to claim 1, wherein $R_3$ is an acyl group of a $C_{1-4}$-hydrocarbon carboxylic or $C_{1-10}$-alkanesulfonic acid.

8. A compound according to claim 1, wherein $R_3$ is an acyl group of a $C_{1-4}$-hydrocarbon carboxylic or $C_{1-4}$-alkanesulfonic acid.

9. A compound according to claim 1, wherein $R_5$ is $C_{3-6}$-cycloalkyl or $C_{3-6}$-cycloalkyl substituted by $C_{1-4}$-alkyl.

10. (5Z, 13E)-(9R,11R,15S)-9-chloro-15-cyclohexyl-11,15-dihydroxy-3-oxa16,17,18,19,20-pentanor-5,13-prostadienoic acid tert-butyl ester, (5Z,13E)-(9R,11R,15S)-9-chloro-15-cyclohexyl-11,15-dihydroxy-3-oxa-16,17,18,19,20-pentanor-5,13-prostadienoic acid, (5Z,13E)-(9S,11R,15S)-9-chloro-15-cyclohexyl-11,15-dihydroxy-3-oxa-16,17,18,19,20-pentanor-5,13-prostadienoic acid, or (5Z,13E)-(9R,11R,15S)-15-cyclohexyl-9-fluro-11,15-dihydroxy-3-oxa-16,17,18,19,20-pentanor-5,13-prostadienoic acid, each a compound of claim 1.

11. A method of achieving a cytoprotective effect in a host comprising administering an effective amount of a compound of the formula

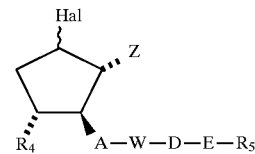

in which

Hal is a chlorine or fluorine atom in alpha or beta position,

Z is

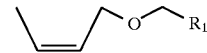

$R_1$ is

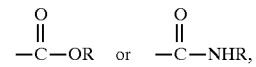

wherein R is (a) hydrogen; (b) C-alkyl; (c) C-alkyl substituted by halogen, $C_{1-4}$-alkoxy, $C_{6-10}$-aryl, $C_{6-10}$-aroyl, $C_{6-10}$-aryl or $C_{6-10}$-aroyl each substituted as defined below for aryl, dialkylamino or trialkylammonium; (d) $C_{3-10}$-cycloalkyl or $C_{3-10}$-cycloalkyl substituted by $C_{1-4}$-alkyl; (e) $C_{6-10}$-aryl or $C_{6-10}$-aryl substituted by 1–3 halogen atoms, phenyl, 1–3 $C_{1-4}$-alkyl groups, chloromethyl, fluoromethyl, trifluoromethyl, carboxyl, hydroxy or $C_{1-4}$-alkoxy; (f) a 5- or 6-membered aromatic heterocyclic ring containing an N, O or S atom;

$R_3$ is an acyl group of a $C_{1-15}$-hydrocarbon carboxylic or sulfonic acid, or a group defined for $R_2$;

A is a —$CH_2$—$CH_2$—, a trans—CH=CH— or —C≡C— group,

W is hydroxymethylene or

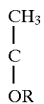

wherein the hydroxy and OR group can be in the alpha or beta position,

D and E together are a single bond;

$R_4$ is OR;

R is H; an acyl group of a $C_{1-5}$-hydrocarbon carboxylic or sulfonic acid; tetrahydropyranyl; tetrahydrofuranyl; alpha-ethoxyethyl; trimethylsilyl; dimethyl tert-butylsilyl; dimethyl hexylsilyl; diphenyl tert-butylsilyl or tribenzylsilyl;

$R_5$ is $C_{3-10}$-cycloalkyl or $C_{3-10}$-cycloalkyl substituted by $C_{1-4}$-alkyl; $C_{6-10}$-aryl or $C_{6-10}$-aryl substituted by 1–3 halogen atoms, phenyl, 1–3 $C_{1-4}$-alkyl, chloromethyl, fluoromethyl, trifluoromethyl, carboxyl, hydroxy or $C_{1-4}$-alkoxy; or a 5- or 6-membered aromatic heterocyclic ring containing a N, O or S atom;

or where $R_2$ is H, a physiologically compatible salt thereof or a cyclodextrin clathrate thereof.

12. A method of inhibiting gastric acid secretion comprising administering an effective amount of a compound of claim 1.

13. A method of achieving an ulcer healing effect comprising administering an effective amount of a compound of claim 1.

14. A method of achieving a luteolytic effect, comprising administering an effective amount of a compound of claim 1.

15. A pharmaceutical composition comprising an effective amount of claim 1 and a pharmaceutically acceptable carrier.

16. A pharmaceutical composition comprising 0.01–100 mg of a compound of claim 1 and a pharmaceutically acceptable carrier.

17. A method according to claim 11, wherein the effective amount is 1–1500 micrograms/kg/day.

18. A method according to claim 14, wherein the effective amount is 1–1500 micrograms/kg/day.

* * * * *

UNITED STATES PATENT AND TRADEMARK OFFICE
CERTIFICATE OF CORRECTION

PATENT NO. : 5,891,910  Page 1 of 2
DATED : April 6, 1999
INVENTOR(S) : Buchmann et al.

It is certified that error appears in the above-identified patent and that said Letters Patent is hereby corrected as shown below:

**On the face of the Patent, in the "[*] Notice" section:** Delete in its entirety

IN THE CLAIMS

Claim 1, line 8: Replace the entire line with:

-- is $-\overset{\overset{\displaystyle O}{\|}}{C}-OR_2$ or $-\overset{\overset{\displaystyle O}{\|}}{C}-NHR_3$, --.

line 9: Replace the entire line with:

-- wherein $R_2$ is (a) hydrogen; (b) $C_{1-10}$-alkyl; (b) $C_{1-10}$-alkyl --.

Claim 11, line 10: Replace the entire line with:

-- is $-\overset{\overset{\displaystyle O}{\|}}{C}-OR_2$ or $-\overset{\overset{\displaystyle O}{\|}}{C}-NHR_3$, --.

UNITED STATES PATENT AND TRADEMARK OFFICE
CERTIFICATE OF CORRECTION

PATENT NO. : 5,891,910
DATED : April 6, 1999
INVENTOR(S) : Buchmann et al.

It is certified that error appears in the above-identified patent and that said Letters Patent is hereby corrected as shown below:

line 11: Replace the entire line with:

-- wherein $R_2$ is (a) hydrogen; (b) $C_{1-10}$-alkyl; (b) $C_{1-10}$-alkyl --.

Signed and Sealed this

Eighth Day of February, 2000

Attest:

Q. TODD DICKINSON

*Attesting Officer*  *Commissioner of Patents and Trademarks*